(12) United States Patent
O'Day et al.

(10) Patent No.: US 9,205,224 B2
(45) Date of Patent: Dec. 8, 2015

(54) INFUSION MECHANISM AND METHOD

(75) Inventors: Therese O'Day, Bloomington, IN (US); Frank J. Fischer, Jr., Bloomington, IN (US); Lindsay Koren, Bloomington, IN (US); Mark Allen Magnuson, Bloomington, IN (US); Richard Earl Luedemann, Ellettsville, IN (US); Shyam Kuppurathanam, Bloomington, IN (US); Keith R. Milner, West Lafayette, IN (US)

(73) Assignee: Cook Medical Technologies, LLC

( * ) Notice: Subject to any disclaimer, the term of this patent is extended or adjusted under 35 U.S.C. 154(b) by 955 days.

(21) Appl. No.: 12/756,400

(22) Filed: Apr. 8, 2010

(65) Prior Publication Data

US 2011/0251588 A1 Oct. 13, 2011

(51) Int. Cl.
 *A61M 25/00* (2006.01)
 *A61M 25/01* (2006.01)
 *A61M 25/09* (2006.01)

(52) U.S. Cl.
 CPC ........... *A61M 25/003* (2013.01); *A61M 25/007* (2013.01); *A61M 25/002* (2013.01); *A61M 25/0108* (2013.01); *A61M 2025/004* (2013.01); *A61M 2025/0073* (2013.01); *A61M 2025/0079* (2013.01); *A61M 2025/0183* (2013.01); *A61M 2025/09175* (2013.01)

(58) Field of Classification Search
 CPC ...................... A61M 2025/0004; A61M 25/00; A61M 25/0023; A61M 2025/0035; A61M 25/0026; A61M 2025/004; A61M 2025/0073; A61M 2025/0079; A61M 2025/0183; A61M 2025/09175; A61M 25/003; A61M 25/007; A61M 25/0108

USPC ........... 604/96.01, 523, 164.01, 264, 48, 246, 604/534
See application file for complete search history.

(56) References Cited

U.S. PATENT DOCUMENTS

| | | | |
|---|---|---|---|
| 4,968,307 A | | 11/1990 | Dake et al. |
| 4,995,865 A | * | 2/1991 | Gahara et al. .................. 604/43 |
| 5,015,232 A | * | 5/1991 | Maglinte .................. 604/102.02 |
| 5,160,325 A | | 11/1992 | Nichols et al. |
| 5,267,979 A | | 12/1993 | Appling et al. |
| 5,405,334 A | | 4/1995 | Roth et al. |
| 5,425,723 A | | 6/1995 | Wang |
| 5,569,215 A | | 10/1996 | Crocker |
| 5,573,520 A | | 11/1996 | Schwartz et al. |
| 5,647,859 A | | 7/1997 | Lampropoulos et al. |
| 5,665,076 A | | 9/1997 | Roth et al. |
| 5,797,886 A | | 8/1998 | Roth et al. |

(Continued)

OTHER PUBLICATIONS

Poulsen, Mottola, Stocker; An In Vitro Comparison of Thrombolytic Infusion Catheters; 1998; pp. 1-8; Merit Medical Systems, Inc.; South Jordan, Utah, U.S.

*Primary Examiner* — Kami A Bosworth
*Assistant Examiner* — Brandy S Lee
(74) *Attorney, Agent, or Firm* — Liell & McNeil

(57) ABSTRACT

An infusion mechanism for treating an intraluminal site in a patient includes an infusion catheter having an elongate body with a proximal body end defining at least one fluid supply orifice, and a distal body end. The elongate body defines a high head loss lumen in fluid communication with a first set of side ports defining a proximal infusion zone. The elongate body further defines a low head loss lumen in fluid communication with a second set of side ports defining a distal infusion zone.

19 Claims, 3 Drawing Sheets

(56) References Cited

U.S. PATENT DOCUMENTS

| | | | |
|---|---|---|---|
| 5,800,408 A * | 9/1998 | Strauss et al. | 604/264 |
| 5,817,072 A | 10/1998 | Lampropoulos et al. | |
| 6,117,125 A | 9/2000 | Rothbarth et al. | |
| 6,179,342 B1 | 1/2001 | Shen | |
| 2003/0093029 A1 * | 5/2003 | McGuckin et al. | 604/43 |
| 2005/0187535 A1 * | 8/2005 | Wilson et al. | 604/523 |
| 2006/0004325 A1 * | 1/2006 | Hamatake et al. | 604/43 |
| 2006/0229573 A1 | 10/2006 | Lamborne | |

* cited by examiner

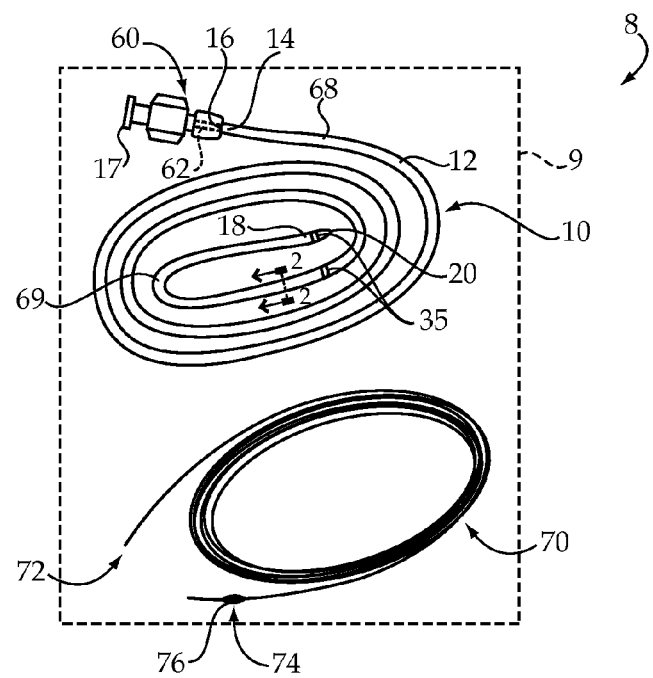
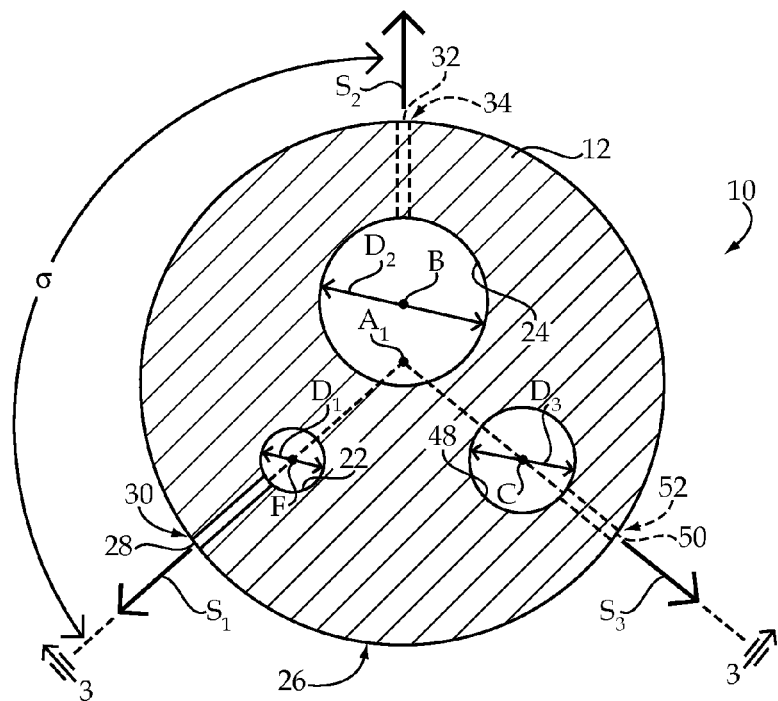
Figure 1
Figure 2

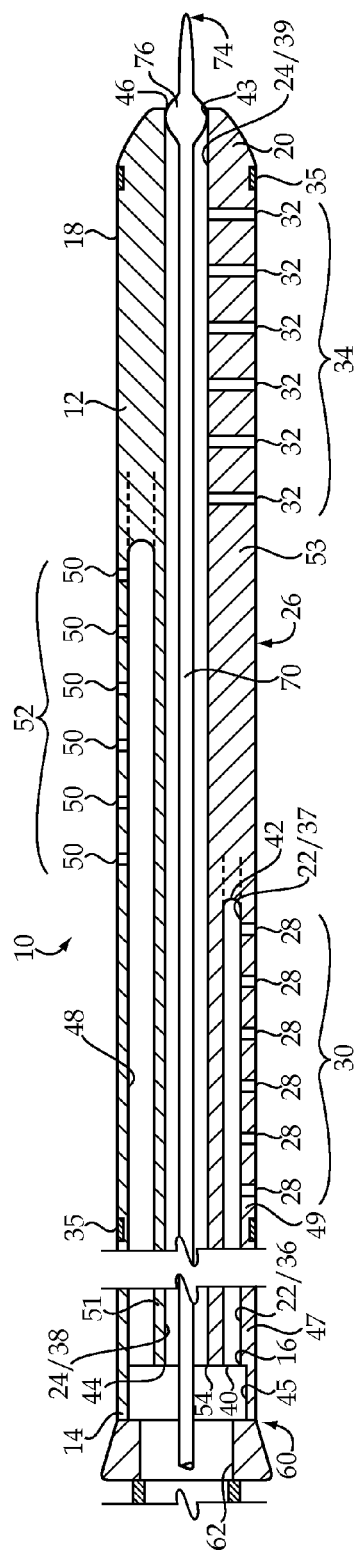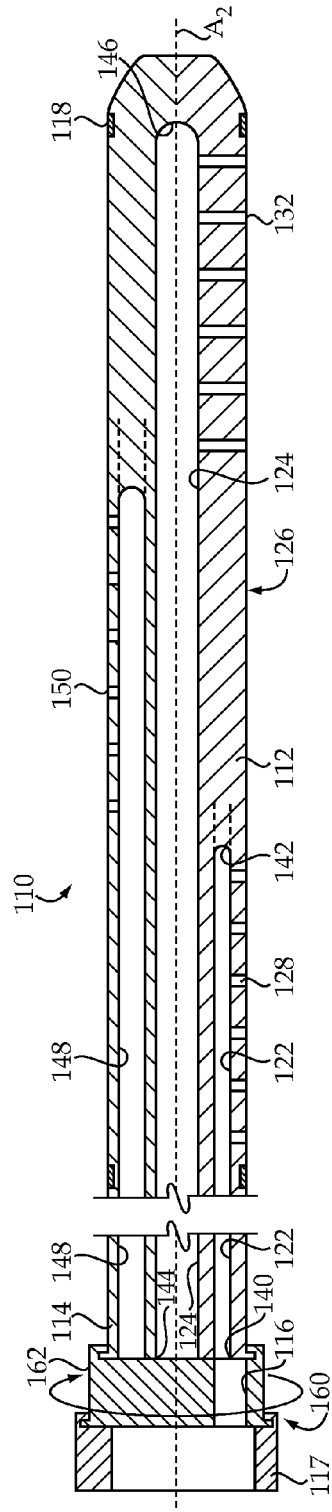
Figure 3
Figure 4

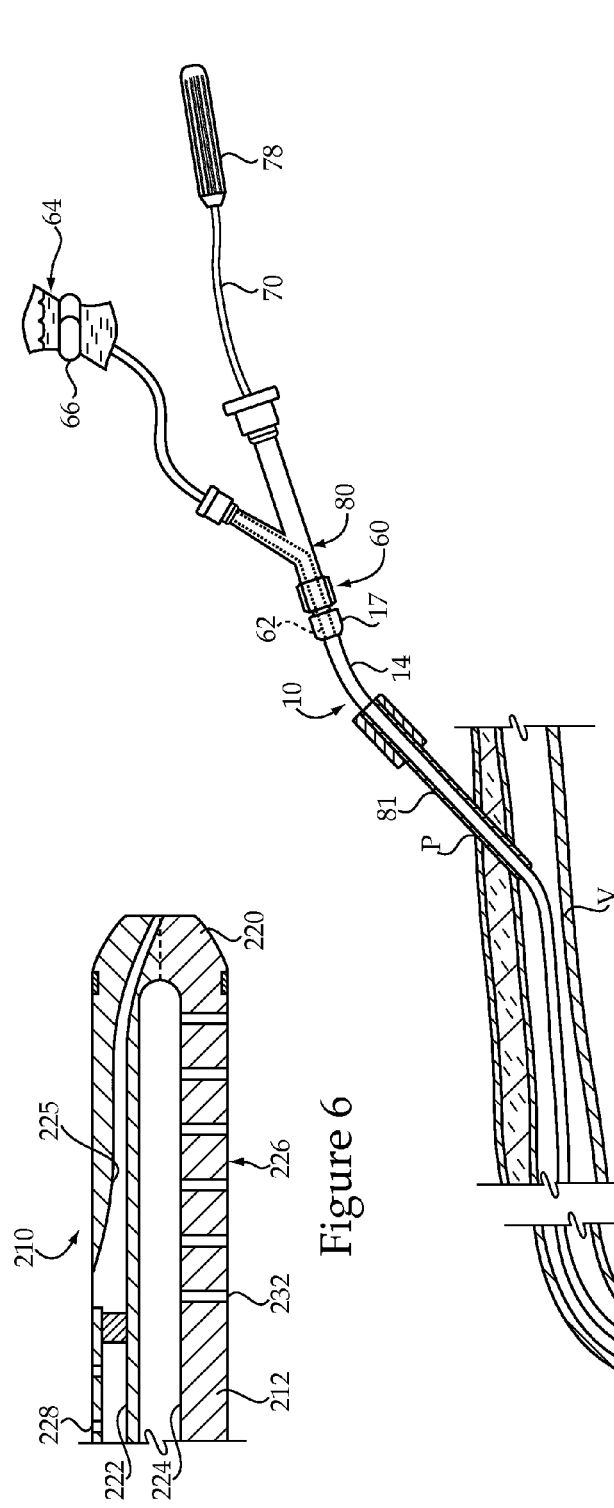
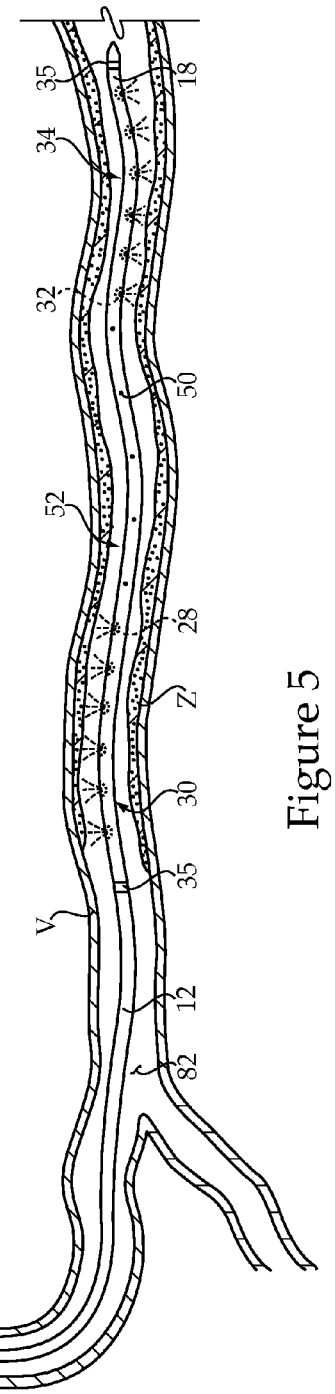
Figure 5
Figure 6

INFUSION MECHANISM AND METHOD

TECHNICAL FIELD

The present disclosure relates generally to infusion mechanisms having an infusion catheter, and relates more particularly to an infusion catheter having multiple lumens imparting differing fluid pressure loss characteristics.

BACKGROUND

Percutaneous access to the cardiovascular system is used to diagnose, evaluate, and treat a variety of conditions. A typical procedure involves passing a wire guide through an opening in a patient's skin which connects to a vascular structure such as a vein or artery. The wire guide can then be passed through the cardiovascular system to a location of interest within the patient. Once the wire guide has been appropriately positioned, a catheter may be passed into the patient and guided by the wire guide to a location where a procedure is to be performed. Angioplasty, imaging, and the placement of stents, graphs, filters and other devices, are common procedures which are performed according to variations of the above general technique. It is also common to use percutaneous access for the placement of catheters which deliver fluid at an intraluminal treatment site. Devices known as infusion catheters are commonly used to deliver a therapeutic treatment fluid such as a thrombolytic agent to a clot or the like within a vein or artery.

A wide variety of infusion catheter designs are known and commercially available. One general class of infusion catheters utilizes a longitudinally extending lumen which connects a supply of therapeutic fluid located outside of the patient with an intraluminal space by way of ports communicating between the lumen and the intraluminal space. Various locations on a patient's body may be used to percutaneously access the cardiovascular system for infusion in this manner. While in some instances a location of interest within the patient can be reached from a nearby access point, in other instances a preferred access point may be relatively farther away. As a result, relatively long infusion catheters are often used, to enable a treatment site within, for example, a patient's torso, to be reached from a relatively remote access point, such as the patient's neck or ankle area.

One problem with conventional infusion catheters may be a difficulty in supplying fluid uniformly along the catheter infusion length. Various strategies, such as non-uniform distribution of the infusion ports, have been suggested to address this challenge, meeting with varying degrees of success. Infusion catheters having multiple lumens for conveying fluid to different sections of the catheter infusion length have also been proposed. These designs are believed to provide for more uniform infusion than is practicable or possible with certain single lumen designs. Even multiple lumen catheters, however, when observed under actual use conditions or in the lab have been discovered to have shortcomings.

SUMMARY OF THE DISCLOSURE

In one aspect, an infusion catheter includes an elongate body defining a longitudinal axis, and including a proximal body end defining at least one fluid supply orifice, and a distal body end which includes a distal tip. The elongate body further defines a high head loss lumen in fluid communication with the at least one fluid supply orifice and extending axially through the elongate body. The elongate body further defines a low head loss lumen in fluid communication with the at least one fluid supply orifice and extending axially through the elongate body. The elongate body further includes an outer surface having a first set of side ports formed therein and defining a proximal infusion zone, and a second set of side ports formed therein and defining a distal infusion zone. The first set of side ports are in fluid communication with the high head loss lumen and the second set of side ports are in fluid communication with the low head loss lumen.

In another aspect, an infusion mechanism for treating an intraluminal site in a patient includes a catheter having an elongate body defining a longitudinal axis, a high head loss lumen and a low head loss lumen, and each of the high head loss lumen and the low head loss lumen extending axially through the elongate body. The infusion mechanism further includes a fluid apportioning mechanism having at least one fluid conduit configured to fluidly connect the high head loss lumen and the low head loss lumen with an extraluminal fluid supply. The elongate body further includes a first body segment coupled with the fluid apportioning mechanism, and a second body segment which includes an infusion segment. The infusion segment includes an outer surface having a plurality of side ports formed therein, the plurality of side ports including a proximal set of side ports in fluid communication with the high head loss lumen, and a distal set of side ports in fluid communication with the low head loss lumen.

In still another aspect, a method of conveying a fluid to an intraluminal space includes passing fluid through a high head loss lumen of an infusion catheter, and effusing fluid from a proximal set of side ports fluidly communicating between the high head loss lumen and the intraluminal space. The method further includes passing fluid through a low head loss lumen of the infusion catheter, and effusing fluid from a distal set of side ports fluidly communicating between the low head loss lumen and the intraluminal space.

BRIEF DESCRIPTION OF THE DRAWINGS

FIG. 1 is a diagrammatic view of an infusion mechanism, according to one embodiment;

FIG. 2 is a sectioned view of an infusion catheter according to one embodiment;

FIG. 3 is a sectioned side diagrammatic view of an infusion catheter in two different section planes, taken along line 3-3 of FIG. 2, having a wire guide positioned therein;

FIG. 4 is a sectioned side diagrammatic view of an infusion catheter in two different section planes according to another embodiment;

FIG. 5 is a side diagrammatic view of an infusion mechanism at one stage of a percutaneous procedure; and FIG. 6 is a sectioned side diagrammatic view of a portion of an infusion catheter in two different section planes, according to yet another embodiment.

DETAILED DESCRIPTION

Referring to FIG. 1, there is shown an infusion mechanism 8 for treating an intraluminal site in a patient. Infusion mechanism 8 may include an infusion catheter 10, and a wire guide 70, the infusion catheter 10 and wire guide 70 being positioned within a sterile package 9. Sterile package 9 may include a sealed pouch in one embodiment, and other packaging features such as a tube protector coil for infusion catheter 10 may be included but are not shown in FIG. 1. As will be further apparent from the following description, infusion mechanism 8 may be uniquely configured to address problems associated with fluid pressure losses tending to occur in earlier strategies for delivering a treatment fluid to an intraluminal site in a patient.

Infusion catheter 10 may include an elongate body 12 having a proximal body end 14 and a distal body end 18. A fluid apportioning mechanism 60 such as a manifold, having at least one fluid conduit 62, may be coupled with proximal body end 14 and configured to fluidly connect infusion catheter 10 with an extraluminal fluid supply, as further described herein. A connecting mechanism 17 such as a fitting may be coupled with or part of fluid apportioning mechanism 60, to enable an extraluminal fluid supply to fluidly connect with conduit 62. Elongate body 12 may further include a proximal body segment 69 which is coupled with apportioning mechanism 60 and defines at least one fluid supply orifice 16 fluidly communicating with conduit 62. Elongate body 12 may further include a distal body segment 69 which includes a distal tip 20 positioned at distal body end 18. A set of radiopaque markers 35 may be positioned on or in distal body segment 69 to enable identification of an infusion length of elongate body 12 in a conventional manner.

Wire guide 70 may include a proximal wire guide tip 72, which will typically remain outside of a patient when infusion mechanism 8 is used, and a distal wire guide tip 74 which includes an occlusion bulb 76. In one embodiment, occlusion bulb 76 may be used to block fluid flow out of distal tip 20 during infusing a treatment fluid such as a thrombolytic liquid into a patient, as further described herein.

Referring also to FIG. 2, there is shown a sectioned view of elongate body 12 taken along line 2-2 of FIG. 1. Elongate body 12 may define a longitudinal axis $A_1$ which extends from proximal body end 14 to distal body end 18. Elongate body 12 may further define a high head loss lumen 22 in fluid communication with fluid supply orifice 16, high head loss lumen 22 extending axially through elongate body 12. Elongate body 12 may further define a low head loss lumen 24 in fluid communication with fluid supply orifice 16 and also extending axially through elongate body 12.

Fluids tend to lose pressure as they pass through a fluid conduit. Such pressure losses can result from friction between the fluid and walls of the conduit, friction within the fluid itself, and the geometry of the conduit such as turns. As further explained herein, fluid flowing through high head loss lumen 22 will tend to lose pressure head relatively more rapidly as it travels through elongate body 12 than fluid passing through low head loss lumen 24. Thus, for each "X" cm of flow length, fluid passing through high head loss lumen 22 can be expected to lose a relatively greater amount of head pressure, whereas for each "X" cm of flow length, fluid passing through low head loss lumen 24 can be expected to lose a relatively lesser amount of head pressure. Since high head loss lumen 22 may have a shorter length than high head loss lumen 24, a total head pressure loss between the point at which fluid enters the respective lumens and where it exits the respective lumens may be equal, as further described herein. Elongate body 12 may further include an outer surface 26 having a first set of side ports 28 formed therein which define a proximal infusion zone 30, and a second set of side ports 32 formed therein which define a distal infusion zone 34. First set of side ports 28 may be in fluid communication with high head loss lumen 22, whereas second set of side ports 32 may be in fluid communication with low head loss lumen 24. Elongate body 12 may further define a medium head loss lumen 48 extending axially through elongate body 12, and a third set of side ports 50 formed in outer surface 26 and in fluid communication with medium head loss lumen 48. Side ports 50 may be located axially between first set of side ports 28 and second side ports 32 and may define a middle infusion zone 52.

Referring also now to FIG. 3, high head loss lumen 22 may include a first supply segment 36 defining a relatively lesser hydraulic diameter, and a first infusion segment 37. Low head loss lumen 24 may include a second supply segment 38 defining a relatively greater hydraulic diameter, and a second infusion segment 39. Medium head loss lumen 48 may define a third hydraulic diameter which is greater than the first hydraulic diameter and less than the second hydraulic diameter. As used herein, the term "hydraulic diameter" should be understood to refer to an effective diameter not necessarily the same as the "real" or geometric diameter. In other words, a fluid lumen of a given hydraulic diameter may be expected to impart a loss in head pressure to a fluid passing therethrough which is the same as that imparted by a circular pipe having a real diameter equal to the subject hydraulic diameter. It may thus be understood that fluid lumens 22, 24 and 48 might actually have equal real diameters. But because of differing cross sectional shapes or other features such as differing total wetted surface areas, the presence or absence of turns and even surface texturing of wetted surface areas, the respective fluid lumens could still cause head pressure in fluid passing therethrough to decrease at differing rates. In one example embodiment, low head loss lumen 24 could include a circular cross sectional shape of a given real diameter, and high head loss lumen 22 could have a non-circular cross sectional shape such as a star shape or another polygonal or non-polygonal shape having the same real diameter. In this example, fluid flowing through high head loss lumen 22 could be expected to lose head pressure relatively more rapidly than fluid flowing through low head loss lumen 24, given the relatively greater wetter surface area of high head loss lumen 22 due to its non-circular shape. Those skilled in the art will contemplate a variety of other variables which might be manipulated to impart desired differential rates of head loss.

In other embodiments, the use of different real diameters for the respective lumens 22, 24 and 48 to obtain the differing pressure loss characteristics will be a practical implementation strategy. Accordingly, high head loss lumen 22 may include a relatively lesser real diameter $D_1$ as shown in FIG. 2. Low head loss lumen 24 may include a relatively greater real diameter $D_2$ as also shown in FIG. 2, and medium head loss lumen 48 may include a third real diameter $D_3$ which is greater than real diameter $D_1$ and less than real diameter $D_2$. In the illustrated embodiment, the respective real diameters refer to geometric diameters of lumens 22, 24 and 48 which intersect longitudinal axes F, B and C of lumens 22, 24 and 48 within first supply segment 36, second supply segment 38 and a supply segment of medium head loss lumen 48 (not numbered).

Elongate body 12 may be formed by an extrusion process. Where extrusion is chosen as a manufacturing technique, as well as with other manufacturing strategies, it may be practical to form each of high head loss lumen 22, low head loss lumen 24 and medium head loss lumen 48 with real diameters which are uniform. Thus, supply segment 36 and infusion segment 37 may have a uniform real diameter between a first proximal lumen end 40 and a first distal lumen end 42. A fluid impermeable wall 47 defines supply segment 36, whereas a fluid permeable wall 49 defines infusion segment 37. Similarly, second supply segment 38 and second infusion segment 39 may have a uniform real diameter between a second proximal lumen end 44 and a second distal lumen end 46. A second fluid impermeable wall 51 defines supply segment 38, whereas a second fluid permeable wall 53 defines infusion segment 39. Fluid permeable walls 49 and 53 may be considered permeable by virtue of side ports 28 and 32 located herein.

A variety of different shapes and configurations for side ports 28, 32 and 50 are contemplated within the context of the present disclosure. In one embodiment, first set of side ports 28, second set of side ports 34 and third set of side ports 50 may each include normally open side ports. In other embodiments, some or all of side ports 28, 34 and 50 may include side ports such as slits which are normally closed but open in response to fluid pressure in the corresponding fluid lumen. A number, shape, size and distribution along or about elongate body 12 of each of the sets of side ports 28, 34 and 50 may also be either uniform or non-uniform. Each of the sets of side ports 28, 34 and 50 may include a plurality of side ports, for example each of the respective sets including a number of side ports equal to three or greater. Each of the individual ports of each set may be uniform in size and shape and may be uniformly distributed within the corresponding infusion zone 30, 34 and 52. In one embodiment, each of the sets of side ports may include an axial distribution along outer surface 26, and may be positioned at uniform radial locations. In other words, each of side ports 28 may be located at a first radial location about axis $A_1$, each of side ports 32 may be located at a second radial location about axis $A_1$ and each of side ports 50 may be located at a third radial location about axis $A_1$.

In the FIG. 2 embodiment, side ports 28 may be located, shaped and oriented relative to longitudinal axis $A_1$ such that they define a first average effluent flow direction from outer surface 26, for example an average effluent flow direction indicated by arrow $S_1$ which is normal to outer surface 26. Each of side ports 32 may be located, shaped and oriented relative to longitudinal axis $A_1$ such that they define a second average effluent flow direction from outer surface 26, for example an average effluent flow direction indicated by arrow $S_2$ which is normal to outer surface 26 and different from flow direction $S_1$. A third average effluent flow direction $S_3$ may be associated with side ports 50. The first average effluent flow direction $S_1$ and the second average effluent flow direction $S_2$ may define a radial angle $\Theta$ about longitudinal axis $A_1$. This configuration differs from a configuration where the respective sets of side ports define parallel average effluent flow directions, known from certain earlier designs. The described and illustrated configuration can enable effluent flow from catheter 10 in a relatively more uniform manner than that possible with such earlier designs which may effuse fluid disproportionately towards certain areas of an intraluminal treatment site.

As mentioned above, high head loss lumen 22 may include first proximal lumen end 40 and first distal lumen end 42, whereas low head loss lumen 24 may include second proximal lumen end 44 and second distal lumen end 46. In one embodiment, first distal lumen end 42 may include a blind lumen end, and second distal lumen end 46 may include an open lumen end defining a wire guide opening 43 in distal tip 20. In an embodiment where catheter 10 is formed via an extrusion process, the extrusion may initially include each of lumens 22, 24 and 48, with each of the lumens extending all the way through elongate body 12 and opening at both proximal body end 14 and distal body end 18. As can be noted from the drawings lumens 22, 24 and 48 are beside one another and not coaxial. During manufacturing, one or more of lumens 22, 24 and 48 may be plugged. The respective lumens may be plugged at different axial locations, such that the lumens have different axial lengths in elongate body 12. Portions of lumen 22 and 48 are shown in phantom in FIG. 3 to indicate an approximate location of a plug.

It will be recalled that wire guide 70 may include occlusion bulb 76 located adjacent to distal wire guide tip 74. In one embodiment, catheter 10 may be passed in a proximal to distal direction over wire guide 70 to a location where occlusion bulb 76 blocks low head loss lumen 24 within distal tip 20, approximately as shown in FIG. 3. This configuration allows fluid flow to occur through low head loss lumen 24, but be blocked or substantially blocked at distal tip 20 to enable a desired fluid flow through side ports 32. In other embodiments, further described herein, each of the fluid lumens may include blind distal lumen ends.

As mentioned above, catheter body 12 may define at least one fluid supply orifice located at proximal body end 14. In the FIG. 3 embodiment, a plurality of separate fluid supply orifices are shown, each being associated with one of lumens 22, 24 and 48. Fluid supply orifice 16 fluidly connects with high head loss lumen 22, and a second fluid supply orifice 54 fluidly connects with low head loss lumen 24. A cavity 45 is formed in elongate body 12 and fluidly connects each of lumens 22, 24 and 48 with fluid conduit 62 by way of the corresponding fluid supply orifices. In other embodiments, also described herein, the respective supply orifices may open at proximal body end 14 and cavity 45 omitted.

Referring now to FIG. 4, there is shown an infusion catheter 110 according to another embodiment. Infusion catheter 110 includes an elongate catheter body 112 having a proximal body end 114 and a distal body end 118. Infusion catheter 110 also includes a high head loss lumen 122 having a first proximal lumen end 140 and a first distal lumen end 142. Elongate body 112 also defines a low head loss lumen 124 having a second proximal lumen end 144 and a second distal lumen end 146. A medium head loss lumen 148 may also be defined by elongate body 112. A first set of side ports 128 may be formed in an outer surface 126 and fluidly communicate with high head loss lumen 122, a second set of side ports 132 may also be formed in outer surface 126 and fluidly communicate with low head loss lumen 124, and a third set of side ports 150 may be formed in outer surface 126 and fluidly communicate with medium head loss lumen 148.

Certain similarities between infusion catheter 110 and infusion catheter 10 may be readily noted. Infusion catheter 110 may also differ from infusion catheter 10 in that second distal lumen end 146 of low head loss lumen 124 includes a blind end. In such an embodiment, rather than sliding catheter body 112 over a wire guide, a placement sheath (not shown) may be used, in a known manner to position catheter 110 at an intraluminal treatment site. A fluid apportioning mechanism 160 or manifold may be used with infusion catheter 110 which has certain differences from fluid apportioning mechanism 60 used with infusion catheter 10. In particular, rather than simultaneously supplying fluid to each of the fluid lumens of infusion catheter 110, fluid apportioning mechanism 160 may be configured to selectively supply fluid to one of fluid lumens 122, 124 and 148 at a time. To this end, fluid apportioning mechanism 160 may include a connecting mechanism 117 configured to fluidly connect with an extraluminal fluid supply, and a rotating valve 162 defining a supply orifice 116 which, upon rotation of rotating valve 162, can establish a fluid connection between a selected one of lumens 122, 124 and 148 and an extraluminal fluid supply by way of fluid supply orifice 116 and connecting mechanism 117. When fluid communications are established between the extraluminal fluid supply and a selected one of lumens 124, 122 and 148, the other lumens may be blocked from fluid communication with the extraluminal fluid supply. While infusion catheters 10 and 110 are shown are separate embodiments, it should be appreciated that a rotating valve fluid apportioning mechanism such as that shown with infusion catheter 110 might also be used with infusion catheter 10. Similarly, the simultaneous fluid supply configuration of infusion catheter 10 could be used with infusion catheter 110. Further still, the illustrated and described blind and open configurations for certain of the fluid lumens in catheters 10 and 110 might be modified from that shown.

Turning now to FIG. 6, there is shown a portion of an infusion catheter 210 according to another embodiment. Infusion catheter 210 may be configured as a rapid exchange catheter such that it is unnecessary to pass a wire guide through an entire length of infusion catheter 210 during positioning infusion catheter 210 at an intraluminal treatment site within a patient. To this end, infusion catheter 210 may include an elongate catheter body 212 defining a wire guide lumen 225 which extends only a portion of an axial length of catheter body 212. Catheter body 212 may further include an outer surface 226 having a set of effluent ports 232 formed therein and fluidly communicating with a low head loss lumen 224. A second set of effluent ports 228 fluidly communicate with a high head loss lumen 222. In the embodiment shown, wire guide lumen 225 may include a portion of lumen 222 which is distal of side ports 228, and blocked from fluid communication therewith. Wire guide lumen 225 may open at outer surface 226 to enable a wire guide passed therethrough to exit and/or enter catheter body 212 at a location distal to side ports 228.

INDUSTRIAL APPLICABILITY

During a typical infusion procedure an extraluminal fluid supply is connected with an infusion catheter. The extraluminal fluid supply can include an infusion pump or a gravity fed fluid supply with a pressure cuff, for example. The infusion catheter supplies a treatment fluid to an intraluminal site such as an intravascular site within a patient by way of one or more fluid lumens opening along an infusion length of the catheter. It is known to use a first fluid lumen to supply treatment fluid to a proximal portion of a catheter infusion length, and a second fluid lumen to supply treatment fluid to a more distal portion of a catheter infusion length. Research has revealed that relatively long-term, low pressure infusion may be useful in some instances. A catheter may be left in a patient for five, six, or even greater than twelve hours. Difficulty in adequately supplying treatment fluid to more distal portions of an infusion catheter using conventional delivery techniques has been discovered, however. This difficulty tends to be more acute in infusion catheters having relatively long infusion lengths, which may sometimes approach or exceed one meter.

In recognition of these and other problems, the present disclosure provides a strategy for successfully conveying fluid to an intraluminal space at an acceptable infusion rate regardless of the total infusion length, infusion rate or pressure, and duration of the infusion procedure. Referring now to FIG. 5, there is shown infusion catheter 10 positioned within a vascular structure V of a patient such as a vein or artery. An access opening P has been formed in the patient, and infusion catheter 10 has been passed through the access opening P by way of an introducer sheath 81 or the like. In the embodiment shown, a Y-fitting 80 has been coupled with infusion catheter 10, and provides a fluid connection between manifold 60 and an extraluminal fluid supply 64, thereby enabling a treatment fluid such as a lytic agent to be supplied to each of the fluid lumens of catheter 10. Extraluminal fluid supply 64 may include a pressure cuff 66 or the like, which may be adjusted to provide and/or vary a pressure of fluid supplied to catheter 10. Wire guide 70, shown attached to a handle mechanism 78, also passes through Y-fitting 80 and thenceforth through catheter body 12 in a manner well known in the art. Although not specifically illustrated in FIG. 5, wire guide 70 may be positioned similarly to that illustrated in FIG. 3 such that occlusion bulb 76 blocks wire guide opening 43.

Infusion catheter 10 is shown in FIG. 5 such that an intraluminal treatment site Z within vascular structure V is more or less aligned with an infusion length of catheter body 12 as may be indicated to a clinician by radiopaque markers 35. Intraluminal treatment site Z may include a thrombus, for example, and the treatment fluid may include a liquid thrombolytic agent, however the present disclosure is not thereby limited. With infusion catheter 10 positioned approximately as shown in FIG. 5, treatment fluid may be passed from extraluminal fluid supply 64 through high head loss lumen 22 and low head loss lumen 24. In an embodiment using a medium head loss lumen, treatment fluid may also be passed from extraluminal fluid supply 64 through medium head loss lumen 48. The treatment fluid may be effused from side ports 30, from side ports 32, and also from side ports 50 into an intraluminal space 82. As described herein, effusing treatment fluid may occur from side ports 30 in proximal infusion zone 32, from side ports 32 in distal infusion zone 34, and from side ports 50 in middle infusion zone 52. Blood flow in vascular structure V may be either anterograde, toward distal body end 18, or blood flow may be retrograde. Referring again to FIG. 3, it may be recalled that treatment fluid passing through high head loss lumen 22 may pass through first supply segment 36, and then through first infusion segment 37. Similarly, treatment fluid passing through low head loss lumen 24 may first pass through second supply segment 38 and then through second infusion segment 39.

As discussed above, pressure cuff 66 and/or gravity, or some other device such as an infusion pump, may be used to provide a supply pressure of fluid to infusion catheter 10 from extraluminal fluid supply 64. A supply pressure of fluid supplied to high head loss lumen 22 and low head loss lumen 24 may be the same, regardless of whether fluid is supplied simultaneously to the respective lumens such as in the FIG. 3 embodiment, or separately as in the FIG. 4 embodiment. As also discussed above, a loss in head pressure in the respective lumens will tend to occur as fluid is conveyed through catheter body 12. In certain earlier designs, head losses could result in essentially zero fluid being infused from distal portions of a catheter infusion length. Intraluminal space 82 will typically contain fluid such as blood having a fluid pressure. If head loss during conveying fluid through an infusion catheter is sufficiently high, exit pressure of the treatment fluid may be insufficient in more distal portions of the infusion catheter to overcome the pressure of fluid in an intraluminal space. As alluded to above, long infusion lengths and relatively low infusion pressures may be desirable for some procedures. Although the present disclosure is not thereby limited, it is contemplated to be particularly advantageous for infusion procedures having relatively more gradual fluid delivery over relatively longer periods of time and/or using relatively long infusion lengths. One example application might include an infusion catheter having a total length of approximately 130 centimeters and an infusion length of approximately 50 centimeters, and an infusion duration of twelve hours or longer.

In one embodiment, effusing fluid from side ports 30 may include effusing fluid from a distal-most one of side ports 30 at a first exit pressure, which will be less than the supply pressure. Effusing fluid from side ports 50 may include effusing fluid from a proximal-most one of side ports 50 at a second exit pressure which is less than the supply pressure and equal to or greater than the first exit pressure. In FIG. 5, it may be noted that one of side ports 28 includes a proximal-most location, i.e. the closest one of side ports 28 to proximal end 14. Another one of side ports 28 includes a distal-most one of side ports 28, the closest one of side ports 28 to distal end 18. A similar characterization of side ports 50 and side ports 32 may be made. Effusing fluid in this manner is contemplated to be advantageous over certain prior designs, where each progressively more distal side port could typically be expected to effuse fluid at a progressively lesser exit pressure.

The present description is for illustrative purposes only, and should not be construed to limit the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. An infusion catheter comprising:
    an elongate body defining a longitudinal axis, and including a proximal body end defining a fluid supply orifice, and a distal body end which includes a distal tip;
    the elongate body further defining a high head loss lumen in fluid communication with the fluid supply orifice and extending axially through the elongate body;
    the elongate body further defining a low head loss lumen in fluid communication with the fluid supply orifice, and the low head loss lumen extending axially through the elongate body and being positioned beside the high head loss lumen such that the high and low head loss lumens are not coaxial, and the low head loss lumen being in fluid communication with the high head loss lumen in a fluid apportioning apparatus at the proximal body end; and
    the elongate body further including an outer surface having a first set of side ports formed therein and defining a proximal infusion zone, and a second set of side ports formed therein and defining a distal infusion zone;
    the first set of side ports extending from the high head loss lumen to the outer surface, such that the first set of side ports are in fluid communication with the high head loss lumen;
    the second set of side ports extending from the low head loss lumen to the outer surface, such that the second set of side ports are in fluid communication with the low head loss lumen; and
    the high and low head loss lumens having different effective hydraulic diameters along a segment of the longitudinal axis, and at least one of the high and low head loss lumens having a blind distal lumen end.

2. The infusion catheter of claim 1 wherein:
    the high head loss lumen includes a first supply segment defining a relatively lesser hydraulic diameter, and a first infusion segment; and
    the low head loss lumen includes a second supply segment defining a relatively greater hydraulic diameter, and a second infusion segment.

3. The infusion catheter of claim 2 wherein each of the first set of side ports and the second set of side ports include normally open side ports having an axial distribution along the outer surface, wherein the first set of side ports define a first average effluent flow direction from the outer surface and the second set of side ports define a second average effluent flow direction from the outer surface, the first average effluent flow direction and the second average effluent flow direction defining a radial angle about the longitudinal axis.

4. The infusion catheter of claim 2 wherein:
    the high head loss lumen includes a first proximal lumen end, and a first distal lumen end, the first distal lumen end including a blind lumen end; and
    the low head loss lumen includes a second proximal lumen end, and a second distal lumen end, the second distal lumen end being located in the distal tip and including an open lumen end.

5. The infusion catheter of claim 2 wherein the elongate body further defines a medium head loss lumen in fluid communication with the fluid supply orifice and extending axially through the elongate body, the elongate body further defining a third set of side ports formed in the outer surface and in fluid communication with the medium head loss lumen, the third set of side ports being located axially between the first set of side ports and the second set of side ports and defining a middle infusion zone.

6. The infusion catheter of claim 2 wherein the first supply segment includes a uniform diameter which includes a relatively lesser real diameter, and wherein the second supply segment includes a uniform diameter which includes a relatively greater real diameter.

7. The infusion catheter of claim 1 wherein the at least one fluid supply orifice includes a first fluid supply orifice and a second fluid supply orifice, the first fluid supply orifice opening at the proximal body end and being in fluid communication with the high head loss lumen, and the second fluid supply orifice opening at the proximal body end and being in fluid communication with the low head loss lumen.

8. An infusion mechanism for treating an intraluminal site in a patient comprising:
    a catheter having an elongate body defining a longitudinal axis, a high head loss lumen and a low head loss lumen, and the high head loss lumen and the low head loss lumen extending axially through the elongate body and being positioned beside one another such that the high and low head loss lumens are not coaxial; and
    a fluid apportioning mechanism having at least one fluid conduit fluidly connecting the high head loss lumen with the low head loss lumen, and configured to fluidly connect the high head loss lumen and the low head loss lumen with an extraluminal fluid supply;
    the elongate body further including a proximal body segment coupled with the fluid apportioning mechanism, and a distal body segment, the distal body segment including an outer surface having a plurality of side ports formed therein, the plurality of side ports including a first set of side ports extending from the high head loss lumen to the outer surface such that the first set of side ports are in fluid communication with the high head loss lumen, and a second set of side ports extending from the low head loss lumen to the outer surface such that the second set of side ports are in fluid communication with the low head loss lumen; and
    the high and low head loss lumens having different effective hydraulic diameters along a segment of the longitudinal axis, and at least one of the high and low head loss lumens having a blind distal lumen end.

9. The infusion mechanism of claim 8 wherein the high head loss lumen defines a first hydraulic diameter which includes a relatively lesser hydraulic diameter, and wherein the low head loss lumen defines a second hydraulic diameter which includes a relatively greater hydraulic diameter.

10. The infusion mechanism of claim 9 wherein:
the high head loss lumen includes a first proximal lumen end located within the proximal body segment, and a first distal lumen end located within the distal body segment, the first distal lumen end including a blind lumen end; and
the low head loss lumen includes a second proximal lumen end located within the proximal body segment, and a second distal lumen end located within the distal body segment, the second distal lumen end including a blind lumen end.

11. The infusion mechanism of claim 9 wherein the elongate body further defines a medium head loss lumen defining a third hydraulic diameter which is greater than the first hydraulic diameter and less than the second hydraulic diameter, and the outer surface of the elongate body further having a middle set of side ports formed therein and being in fluid communication with the medium head loss lumen.

12. The infusion mechanism of claim 11 wherein:
the elongate body further includes a proximal body end coupled with the fluid apportioning mechanism, and a distal body end which includes a distal tip, and the elongate body further defining a wire guide opening located in the distal tip; and
one of the high head loss lumen, the low head loss lumen and the medium head loss lumen including a wire guide lumen fluidly connecting with the wire guide opening within the distal tip.

13. The infusion mechanism of claim 12 further comprising a wire guide having a proximal wire guide tip and a distal wire guide tip, the distal wire guide tip including an occlusion bulb configured to block the wire guide opening.

14. A method of conveying a fluid to an intraluminal space for treating an intraluminal site in a patient comprising the steps of:
fluidly connecting a high head loss lumen and a low head loss lumen each formed in an elongate body of an infusion catheter with an extraluminal fluid supply via at least one fluid conduit of a fluid apportioning mechanism, where the high head loss lumen is in fluid communication with the low head loss lumen via the at least one fluid conduit;
the elongate body defining a longitudinal axis and each of the high head loss lumen and the low head loss lumen extending axially through the elongate body, and the elongate body including a proximal body end defining at least one fluid supply orifice fluidly connecting the at least one fluid conduit with the high head loss lumen and the low head loss lumen, and a distal body end having a distal tip;
passing the fluid through the high head loss lumen such that the fluid is conveyed into a proximal set of side ports opening within the high head loss lumen and defining a proximal infusion zone;
effusing the fluid from outlets of the proximal set of side ports formed in an outer surface of the elongate body into the intraluminal space;
passing the fluid through the low head loss lumen such that the fluid is conveyed into a distal set of side ports opening within the low head loss lumen and defining a distal infusion zone; and
effusing the fluid from outlets of the distal set of side ports formed in the outer surface of the elongate body into the intraluminal space.

15. The method of claim 14 wherein:
the step of passing fluid through the high head loss lumen further includes passing the fluid through a supply segment of the high head loss lumen defined by a fluid impermeable wall, then passing the fluid through an infusion segment of the high head loss lumen defined by a fluid permeable wall wherein the proximal set of side ports are located; and
the step of passing fluid through the low head loss lumen further includes passing the fluid through a supply segment of the low head loss lumen defined by a fluid impermeable wall, then passing the fluid through an infusion segment of the low head loss lumen defined by a fluid permeable wall wherein the distal set of side ports are located.

16. The method of claim 15 further comprising a step of supplying fluid to each of the high head loss lumen and the low head loss lumen at a supply pressure;
the step of effusing fluid from the proximal set of side ports further including effusing fluid from a distal-most one of the proximal set of side ports at a first exit pressure which is less than the supply pressure; and
the step of effusing fluid from the distal set of side ports further including effusing fluid from a proximal-most one of the distal set of side ports at a second exit pressure which is less than the supply pressure and equal to or greater than the first exit pressure.

17. The method of claim 16 wherein each of the effusing steps includes effusing a treatment fluid into an intraluminal space of a body lumen of a patient.

18. The method of claim 17 wherein each of the effusing steps further includes effusing a lytic agent at an intravascular site within the patient.

19. An infusion mechanism comprising:
an infusion catheter that includes a manifold attached to a proximal body end of an elongate body, and the elongate body defines a plurality of lumens that are fluidly connected to the manifold, and each of the plurality of lumens being fluidly connected to a respective one of a plurality of sets of side ports that open through an outer surface of the elongate body;
a liquid thrombolytic agent supply fluidly connected to the manifold;
each of the respective sets of side ports being different distances from the proximal body end along a longitudinal axis of the elongate body;
the plurality of lumens include a low head loss lumen and a high head loss lumen having different effective hydraulic diameters;
the low head loss lumen being fluidly connected to one of the sets of side ports that is distal to an other one of the sets of side ports, which is fluidly connected to the high head loss lumen.

* * * * *